(12) United States Patent
Al-Rabiah et al.

(10) Patent No.: US 8,101,805 B2
(45) Date of Patent: Jan. 24, 2012

(54) LOW PRESSURE ONE-STEP GAS-PHASE PROCESS FOR PRODUCTION OF METHYL ISOBUTYL KETONE

(75) Inventors: Abdulrahman A Al-Rabiah, Riyadh (SA); Abdulaziz A Bagabas, Riyadh (SA); Akhmedov Vagif Malik, Baku, AZ (US)

(73) Assignee: King Abdulaziz City for Science and Technology (KACST), Riyadh (SA)

( * ) Notice: Subject to any disclaimer, the term of this patent is extended or adjusted under 35 U.S.C. 154(b) by 0 days.

(21) Appl. No.: 13/154,475

(22) Filed: Jun. 7, 2011

(65) Prior Publication Data
US 2011/0237837 A1    Sep. 29, 2011

Related U.S. Application Data

(63) Continuation-in-part of application No. 13/091,089, filed on Apr. 20, 2011, now abandoned.

(51) Int. Cl.
*C07C 45/82* (2006.01)
*C07C 45/84* (2006.01)
(52) U.S. Cl. .................................. 568/388; 568/392
(58) Field of Classification Search ............... 568/388, 568/392
See application file for complete search history.

(56) References Cited

U.S. PATENT DOCUMENTS

| 3,666,816 A | 5/1972 | Takagi et al. |
| 3,953,517 A | 4/1976 | Schmitt et al. |
| 4,163,696 A | 8/1979 | Wong |
| 6,008,416 A | 12/1999 | Lawson et al. |
| 6,762,328 B2 | 7/2004 | Saayman et al. |
| 7,671,239 B2 | 3/2010 | Hahn et al. |

*Primary Examiner* — Sikarl Witherspoon
(74) *Attorney, Agent, or Firm* — Geeta Kadambi; Riddhi IP LLC

(57) ABSTRACT

A low-pressure one-step gas-phase process for the production and recovery of methyl isobutyl ketone (MIBK) is disclosed. One-step gas-phase synthesis of MIBK from acetone and hydrogen over nano-Pd/nano-$ZnCr_2O_4$ catalyst at atmospheric pressure is used as an example. The said process is designed to recover the additional heat associated with the reactor effluent via heating acetone feed and recycle (mixed acetone) before entering the reactor. A compressor is introduced to the gas-phase process to increase slightly the reactor effluent pressure before this effluent is cooled and fed to a flash drum. The compressed reactor effluent is used to preheat hydrogen feed and recycle (mixed hydrogen) before entering the reactor. The separation scheme of low-pressure one-step gas-phase process comprises of several distillation columns used for MIBK separation and purification.

12 Claims, 3 Drawing Sheets

LOW PRESSURE ONE-STEP GAS-PHASE PROCESS FOR PRODUCTION OF METHYL ISOBUTYL KETONE

CROSS REFERENCE TO RELATED APPLICATION

This application is a continuation-in-part application and claims priority to U.S. patent application Ser. No. 13/091,089 filed on 20 Apr. 2011, which is a continuation of U.S. patent application Ser. No. 12/856,653 filed on Aug. 15, 2010. The pending U.S. Application 13/091089 is hereby incorporated by reference in its entireties for all of its teachings.

FIELD OF THE INVENTION

This disclosure generally relates to a low pressure one-step gas-phase process for manufacturing methyl isobutyl ketone (MIBK) from acetone and hydrogen.

BACKGROUND

Methyl isobutyl ketone (MIBK) is an important solvent in many chemical industries. MIBK is produced from acetone and hydrogen in a three-step process through diacetone alcohol (DAA) and mesityl oxide (MO) intermediates. MIBK is also manufactured from acetone and hydrogen in a one-step liquid phase process, which is commercially preferred over the three-step process since it offers lower capital investment and operating costs. It also avoids the low conversion of acetone in the first reactor as well as the reversion of mesityl oxide to acetone in the second reactor which are experienced in the three-stage process. The commercial one-step MIBK reactor is operated at liquid phase by contacting acetone and hydrogen at high pressure which ranges between 30-100 atm.

In the commercial MIBK one-step liquid phase process, hydrogen and acetone are passed over metal solid base catalysts at moderate temperatures and high pressure. MIBK is produced with other products and then recovered using four distillation columns wherein the first column removes light hydrocarbons and the second distillation column recycles unconverted acetone. A decanter is then located upstream of the last two columns and is used to separate an aqueous phase. The third column removes propanol-water mixture while the last column separates a purified MIBK as distillate and heavy products including diisobutyle ketone (DIBK) as bottoms stream. In other processes, three distillation columns are used for separating MIBK from other products in which acetone is separated in the first distillation column and recycled back to the reactor.

Although the commercial one-step liquid phase process has many advantages over the three-step process, it still has some disadvantages since the reactor is operated at high pressure with acetone conversion in the range of 35% to 40%. The high pressure process increases both the capital and operating costs of the plant. In addition, the low conversion of acetone increases the recycle-flows and thus equipment sizes of the plant.

SUMMARY

This disclosure describes an apparatus, a method and a process for low-pressure one-step gas-phase acetone self-condensation. In one embodiment, a low-pressure one-step gas-phase process, used for manufacturing MIBK and other products from acetone and hydrogen, is described.

In one embodiment, an apparatus for one-step gas-phase process for MIBK and other products is disclosed. In one embodiment, fresh acetone feed and recycled acetone are mixed (mixed acetone) and heated up via the reactor effluent. In one embodiment, a compressor is introduced to the process to increase the pressure of the reactor effluent. In another embodiment, fresh hydrogen feed and recycled hydrogen are mixed (mixed hydrogen) and heated up via the compressed reactor effluent. In one embodiment, compression and cooling of the reactor effluent enable the separation of unconverted hydrogen from other products in a flash drum. In another embodiment, heat exchangers are introduced to enable heat recovery between the reactor effluent and both mixed acetone and mixed hydrogen streams.

In one embodiment, a catalyst is used to obtain a high yield of MIBK using the one step gas phase acetone self-condensation process. In another embodiment, nano-crystalline zinc chromite supported nano-palladium (nano-Pd/nano-$ZnCr_2O_4$) is used as a catalyst to produce MIBK and other products. The products may at least one of methyl isobutyl ketone (MIBK), Diisobutyl ketone (DIBK), mesityl oxide (MO), mesitylene (M), isopropyl alcohol (IPA) and other products. In another embodiment, one-step gas-phase process to produce MIBK is performed at low-pressure. In one embodiment, the MIBK produced using this one-step gas-phase acetone condensation process has an acetone conversion between 20-78% and MIBK selectivity between 40-73%. In one embodiment, the reaction temperature for the MIBK production process is between 200-350° C.

The novel process of low-pressure one-step gas-phase self-condensation of acetone, method of using and the use of the novel catalyst as well as modifying the apparatus for the process flow to produce MIBK and other products are disclosed herein and may be implemented in any means for achieving various aspects. Other features will be apparent from the accompanying figures and from the detailed description that follows.

BRIEF DESCRIPTION OF THE DRAWINGS

Example embodiments are illustrated by way of example and no limitation in the tables and in the accompanying figures, like references indicate similar elements and in which.

DETAILED DESCRIPTION

Several examples for simulation of one-step gas-phase process, one-step gas-phase acetone condensation apparatus and process recycling acetone under low pressure and utilizing a novel catalyst to produce MIBK using one-step gas phase process are disclosed. Although the present embodiments have been described with reference to specific example embodiments, it will be evident that various modifications and changes may be made to these embodiments without departing from the broader spirit and scope of the various embodiments.

Figure 1:
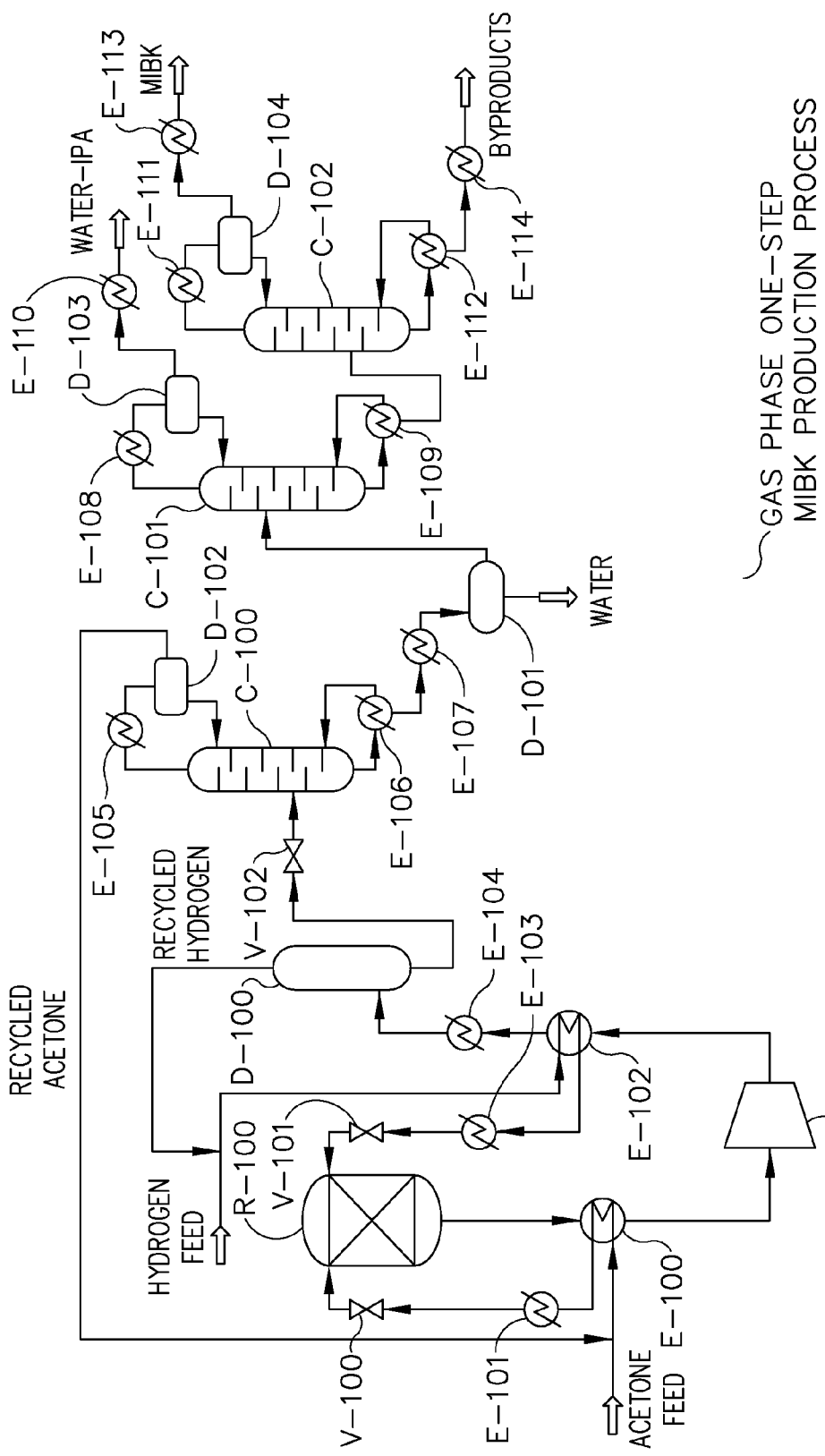
FIG. 1 represents a simplified flow diagram of the process for production of methyl isobutyl ketone via gas-phase one-step acetone self-condensation.

One-Step Gas-Phase Process:

This disclosure reveals a process flow diagram suitable for MIBK production using low-pressure gas-phase one-step of acetone self-condensation which operates. The schematic flow diagram of apparatus used for producing MIBK is shown in FIG. 1. The process is based on gas-phase reaction using selective catalyst which converts acetone and hydrogen into MIBK. The nano-crystalline zinc oxide-based catalyst is one of the examples of selective nano catalyst having a platinum group metal which can be used for production of MIBK.

FIG. 1 is a simplified flow diagram of the entire one-step gas-phase MIBK production process. FIG. 1 shows that recycled acetone is mixed with acetone feed (mixed acetone) and sent for heating in heat-exchanger E-100. Trace water can be removed from the acetone that is being recycled by adding a dryer before mixing with the fresh acetone. Most of the heat associated with the reactor effluent is recovered in heat-exchanger E-100. Acetone feed (mixed acetone) is further heated in heat-exchanger E-101 and then sent to pressure-reducing valve V-100 to adjust the feed pressure before entering reactor R-100.

Reactor R-100 may be operated at different temperatures which may range between 200° C. and 350° C. depending on the type of catalyst. For nano Pd/nano-$ZnCr_2O_4$ catalyst, it is preferable to operate the reactor at high temperature (e.g. 350° C.) to reach a high acetone conversion and high selectivity of MIBK (as shown in Table 10). The reactor pressure is around atmospheric pressure. The reactor pressure may be slightly increased (e.g. 2 atm) depending on the operating conditions of the catalyst used. The gas-phase process scheme is valid for either atmospheric or low pressure reactor.

Reactor R-100 is heat integrated with heat exchangers E-100 (first heat-exchanger) and E-102 (second heat-exchanger). A vacuum pump or blower may be used after the reactor to slightly increase the pressure of reactor effluent before entering heat-exchanger E-100. Most of the heat associated with the reactor effluent is recovered via heating acetone feed (mixed acetone) in heat-exchanger E-100. Steam may be utilized for further heating mixed acetone and mixed hydrogen before entering reactor R-100. The steam temperature is determined based on the reactor conditions.

Fresh and recycled hydrogen streams are mixed and then preheated in heat-exchanger E-102. Heat exchanger E-103 (third heat-exchanger) may be used for heating hydrogen if the required temperature could not be achieved via heat-exchanger E-102. Hydrogen (fresh) feed is then sent to pressure-reducing valve V-101 to adjust hydrogen pressure before entering the reactor (R-100).

The reactor effluent is then compressed in gas compressor K-100 to a low pressure before it is sent to heat-exchanger E-102 and then heat-exchanger E-104 (fourth heat-exchanger) for further cooling. The compressor is only required when the operating pressure of reactor is low. The compressor can also be replaced with a cryogenic cooling system. Compression and cooling of the reactor effluent will permit hydrogen to be separated from other products in flash drum D-100. Acetone and other products are separated as liquid bottoms stream in flash drum D-100 which is then sent to distillation column C-100 for acetone separation.

The feed pressure to distillation column C-100 may be adjusted through pressure-reducing valve V-102. The unconverted acetone is separated as overhead in distillation column C-100. The separated acetone is recycled back to reactor R-100. Other products and MIBK are separated as bottoms stream and then sent to heat-exchanger E-107 for cooling. The product stream is then sent to water decanter (D-101) to separate most of water in an aqueous phase (e.g. 90 wt % of water).

The products are then sent to a second distillation column (C-101) for separation of isopropyl alcohol (IPA) and water from MIBK and other heavy products. The bottoms stream of column C-101 is sent to a third distillation column (C-102) for purifying MIBK. Other heavy products which include mainly diisobutyle ketone (DIBK), mesityl oxide (MO), mesitylene (M) and diacetone alcohol (DA) are separated as bottoms in column C-102. MIBK of high purity (99 wt % min) is recovered in distillation column C-102. All products may be cooled down to 30° C. in heat-exchangers E-110, E-113 and E-114.

Figure 2:
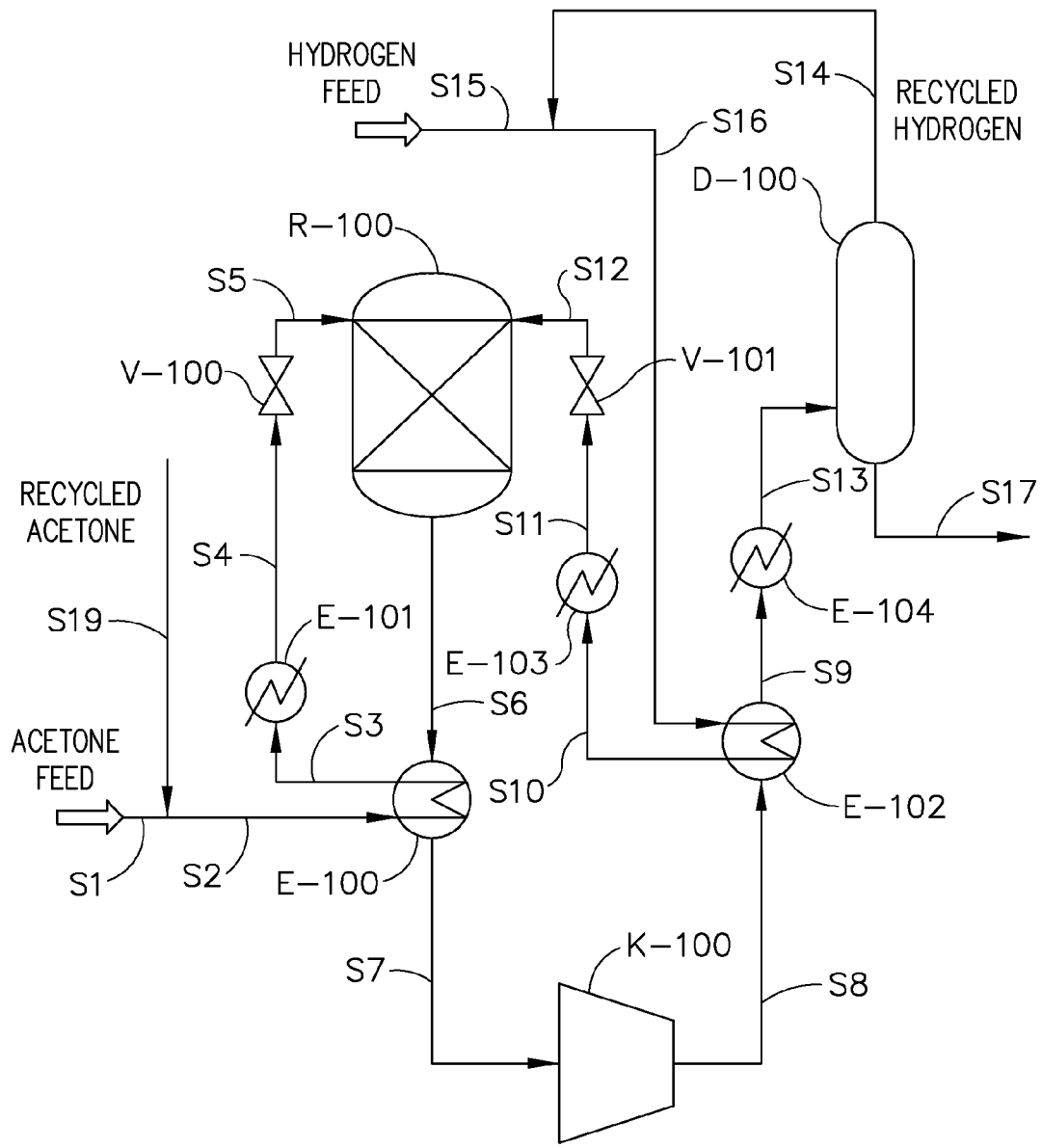
FIG. 2 shows a simplified flow diagram of the gas-phase section of methyl isobutyl ketone production process.

The gas-phase section of MIBK process is further illustrated in FIG. 2. Acetone feed S1 and recycled acetone S19 are mixed and then sent to heat-exchangers E-100 and E-101 for heating. Acetone feed S1 may be entered as gas or liquid stream. It is preferably to enter acetone as liquid stream to recover most of heat associated with reactor effluent stream S6. The fresh and recycled acetone may be mixed at a temperature ranges between 75-80° C. and pressure ranges between 1.5-3 atm. The hot feed S3 is further heated in heat exchanger E-101 to the reactor temperature. The pressure of hot acetone stream S4 may be adjusted using pressure-reducing valve V-100. Acetone stream S5 is then fed to reactor R-100 where the gas-phase reaction is occurred.

Hydrogen feed S15 and recycled hydrogen S14 may be mixed at a temperature of about 35° C. and pressure of about 6 atm. The temperature and pressure of hydrogen feed (S15) are determined based on the conditions of recycled hydrogen (S14).

Hydrogen stream S-16 is heated via hot effluent (S8) which leaves compressor K-100. The outlet temperature of hydrogen stream S10 is a dependent of the inlet temperature of hot effluent (S8). Stream S10 is further heated in heat-exchanger E-103 before it enters reactor R-100. As it is in the case of acetone, valve V-101 is used to reduce pressure of hydrogen stream S12 before it enters reactor R-100.

Reactor R-100 is operated in a gas phase and atmospheric or low pressure. The reaction inside reactor R-100 is exothermic. Cooling water (CW) may be used to operate the reactor isothermally. Most of catalysts are optimally operated at certain temperatures and pressures. The reactor which is operated in gas-phase could be designed in different configurations (e.g. fixed-bed reactor). The mole ratio of hydrogen to acetone feed (mixed acetone) may range between 1 and 6 depends on the used catalyst and operating conditions.

The reactor effluent (S6), which includes MIBK and other products as well as unconverted acetone and hydrogen, is cooled in heat-exchanger E-100 to a temperature between 80 to 100° C. A vacuum pump or blower may be used before unit E-100 when the reactor is operated at atmospheric pressure. The reactor effluent (S6) is then sent to compressor K-100 to increase the effluent pressure. The reactor effluent pressure is increased slightly to permit hydrogen separation from other products in flash drum (D-100). The temperature of compressed reactor effluent (S8) is reduced in heat-exchanger E-102 by cooling hydrogen stream S9. Stream S9 is further cooled via heat-exchanger E-104. Cooling water (CW) may be used for cooling stream S9 in heat-exchanger E-104. The effluent temperature of stream S13 depends on the inlet temperature of cooling water (CW). It is preferred that stream S13 is cooled below 35° C. before sending to flash drum D-100.

Stream S13 is passed to unit D-100 for separating hydrogen as overhead (S14) and other products as bottoms. Recycled hydrogen (S14) is mixed with fresh hydrogen S15 and then sent to heat-exchanger E-102.

Figure 3:
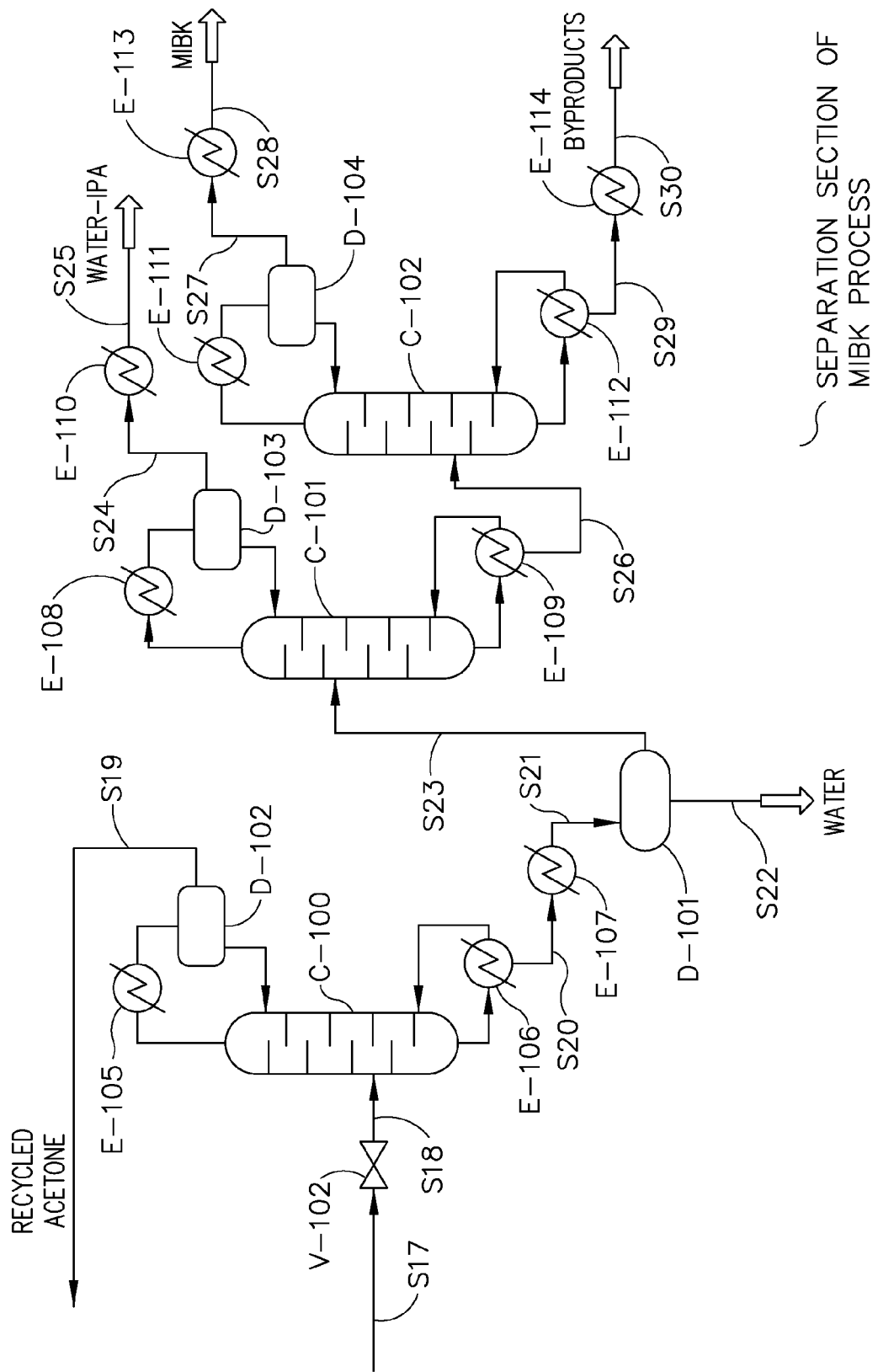
FIG. 3 shows a simplified flow diagram of the separation section of methyl isobutyl ketone production process.

The separation section of MIBK process is illustrated in FIG. 3. The section includes mainly three or four distillation columns. Three distillation columns are shown in FIG. 3 with the assumption that there are no light hydrocarbons associated with the reactor effluent. FIG. 3 shows that the unconverted acetone and other products in stream S17 are separated in distillation column C-100. The pressure of stream S17 may be reduced to less than 2 atm via pressure-reducing valve V-102. The distillation column is used to separate acetone as distillate stream S19 which is then recycled to reactor R-100. The condenser E-105 is used for cooling the overhead acetone which is then passed to reflux drum D-102. The bottoms stream S20 is cooled in heat-exchanger E-107 to a temperature of about 70° C. Stream S20 is then passed to a water decanter (D-101) for separating most of water as aqueous stream S22. Stream S23 which contains products is fed to distillation column C-101 for separating water and isopropyl alcohol (IPA) as distillate which is cooled further in heat-exchanger E-110. Bottoms stream S26 is fed to distillation column C-102 for separating MIBK from other products using condenser E-111 and reflux drum D-104. The purified MIBK stream (S27) is cooled in heat-exchanger E-113 before sending to storage. The outlet stream of reboiler E-112 contains all remaining heavy products such as DIBK which is sent to heat-exchanger E-114 for cooling.

EXAMPLES

The description of low-pressure gas-phase one-step MIBK production process is now further described by means of the following examples, which are intended to be illustrative of the description, but are not intended to limit the scope or underlying principles.

Example 1

A computer calculation was performed to illustrate the process of the description using the gas-phase one-step process. The process was carried out as shown in FIG. 1. The stream numbers correspond to FIG. 2 and FIG. 3. The catalyst used as an example in the simulation is nano-Pd/nano-ZnCr$_2$O$_4$. The mole ratio of hydrogen to acetone before entering the reactor (R-100) is 2. The reaction is carried out in gas-phase at a temperature of 350° C. and atmospheric pressure. For the given conditions, the conversion of acetone is about 77.3% and the MIBK selectivity is about 72.1%.

Acetone feed S1 is entered at 70° C. and 1.8 atm (liquid phase) and mixed with recycled stream S19 which is entered at 74° C. and 1.8 atm. The mixed acetone stream S3 is heated to 324° C. in E-100 and then further heated to 350° C. in E-101. Acetone stream S5 is entered to the reactor at 350° C. and 1 atm. The reactor effluent is cooled in E-101 to 80° C. The effluent stream S7 is compressed in K-100 to 6.5 atm before it is cooled in E-102 from 222° C. to 155° C. Stream S9 is further cooled in unit E-104 to 35° C. and then passed to D-100. Hydrogen is separated in D-100 and recycled at 35° C. and 5.9 atm. The recycled stream S14 is mixed with fresh hydrogen S15 and heated in E-102 to 210° C. Hydrogen stream S10 is further heated in E-103 to 350° C. and then passed through V-101 to decrease pressure before entering R-100. Simulation results of the gas-phase section are summarized in Table 1 and Table 2.

TABLE 1

| | Stream No. | | | | | |
|---|---|---|---|---|---|---|
| | S1 | S2 | S3 | S4 | S6 | S8 |
| Molar flow kmol/h | 100 | 127.2 | 127.2 | 127.2 | 340.7 | 340.7 |
| Mass flow kg/h | 5808 | 7305.3 | 7305.3 | 7305.3 | 8180.3 | 8180.3 |
| Temp C. | 70 | 74.2 | 324.1 | 350 | 350 | 221.5 |
| Pressure atm | 1.8 | 1.8 | 1.4 | 1.2 | 1 | 6.5 |
| Vapor mole fraction | 0 | 0.203 | 1 | 1 | 1 | 1 |
| Component mole % | | | | | | |
| Hydrogen | 0 | 0.02 | 0.02 | 0.02 | 60.96 | 60.96 |
| Acetone | 100 | 98.39 | 98.39 | 98.39 | 8.6 | 8.6 |
| MIBK | 0 | 0 | 0 | 0 | 10.77 | 10.77 |
| Water | 0 | 1.6 | 1.6 | 1.6 | 15.52 | 15.52 |
| Diacetone Alcohol (DA) | 0 | 0 | 0 | 0 | 0.6 | 0.6 |
| Mesityl Oxide (MO) | 0 | 0 | 0 | 0 | 0.33 | 0.33 |
| Mesitylene (M) | 0 | 0 | 0 | 0 | 0.27 | 0.27 |
| Isopropanol (IPA) | 0 | 0 | 0 | 0 | 1.64 | 1.64 |
| Diisobutyl Ketone (DIBK) | 0 | 0 | 0 | 0 | 1.32 | 1.32 |

TABLE 2

| | Stream No. | | | | | |
|---|---|---|---|---|---|---|
| | S9 | S10 | S11 | S13 | S14 | S15 |
| Molar flow kmol/h | 340.7 | 265.2 | 265.2 | 340.7 | 214.7 | 50.5 |
| Mass flow kg/h | 8180.3 | 875.7 | 875.7 | 8180.3 | 773.7 | 101.8 |
| Temp C. | 155 | 210 | 350 | 35 | 35 | 25 |
| Pressure atm | 6.1 | 5.5 | 5.2 | 5.9 | 5.9 | 5.9 |
| Vapor mole fraction | 1 | 1 | 1 | 0.6301 | 1 | 1 |
| Component mole % | | | | | | |
| Hydrogen | 60.96 | 97.36 | 97.36 | 60.96 | 96.74 | 100 |
| Acetone | 8.6 | 1.47 | 1.47 | 8.6 | 1.81 | 0 |
| MIBK | 10.77 | 0.27 | 0.27 | 10.77 | 0.34 | 0 |
| Water | 15.52 | 0.8 | 0.8 | 15.52 | 0.99 | 0 |
| Diacetone Alcohol (DA) | 0.6 | 0 | 0 | 0.6 | 0 | 0 |
| Mesityl Oxide (MO) | 0.33 | 0 | 0 | 0.33 | 0.01 | 0 |
| Mesitylene (M) | 0.27 | 0.01 | 0.01 | 0.27 | 0.01 | 0 |
| Isopropanol (IPA) | 1.64 | 0.08 | 0.08 | 1.64 | 0.1 | 0 |
| Diisobutyl Ketone (DIBK) | 1.32 | 0.01 | 0.01 | 1.32 | 0.01 | 0 |

Table 3 shows simulation results of the separation section which was discussed before.

TABLE 3

| | S18 | S20 | S23 | S24 | S26 | S27 | S29 |
|---|---|---|---|---|---|---|---|
| | \multicolumn{7}{c}{Stream No} | | | | | | |

| | S18 | S20 | S23 | S24 | S26 | S27 | S29 |
|---|---|---|---|---|---|---|---|
| Molar flow kmol/h | 126.1 | 98.9 | 55 | 10.8 | 44.2 | 35.3 | 8.9 |
| Mass flow kg/h | 7406.6 | 5909.3 | 5119.3 | 459.2 | 4660.1 | 3534.3 | 1125.9 |
| Temp C. | 35.1 | 108.1 | 70 | 94.9 | 151.8 | 146.2 | 192.7 |
| Pressure atm | 1.8 | 2.3 | 1.7 | 1.7 | 2.2 | 2.2 | 2.7 |
| Vapor mole fraction | 0 | 0 | 0 | 1 | 0 | 0 | 0 |
| Component mole % | | | | | | | |
| Hydrogen | 0 | 0 | 0 | 0 | 0 | 0 | 0 |
| Acetone | 20.15 | 0.26 | 0.46 | 2.35 | 0 | 0 | 0 |
| MIBK | 28.53 | 36.38 | 65.38 | 3.32 | 80.57 | 99.81 | 4.01 |
| Water | 40.26 | 49.29 | 8.86 | 45.01 | 0.01 | 0.01 | 0 |
| Diacetone Alcohol | 1.62 | 2.07 | 3.72 | 0 | 4.63 | 0 | 23.05 |
| Mesityl Oxide | 0.87 | 1.11 | 1.99 | 0 | 2.48 | 0.03 | 12.24 |
| Mesitylene | 0.71 | 0.91 | 1.63 | 0.02 | 2.03 | 0 | 10.1 |
| Isopropanol | 4.27 | 5.45 | 9.79 | 49.29 | 0.12 | 0.15 | 0 |
| Diisobutyl Ketone | 3.56 | 4.54 | 8.16 | 0 | 10.16 | 0 | 50.6 |

The heat duties of main heat exchangers in the gas-phase section are summarized in Table 4. Table 4 shows that the required heat duty for increasing acetone temperature from 74.2° C. to 350° C. is about 6271 MJ/hr. This value equals the combined heat duties of E-100 (5867 MJ/hr) and E-101 (404 MJ/hr). This shows that the required steam for heating acetone feed (mixed acetone) could be reduced by 93.6%, due to heat integration between the reactor effluent and acetone feed (mixed acetone). Similarly, the required steam for heating hydrogen via E-102 is reduced by 55%.

TABLE 4

| Heat Exchanger | E-100 | E-101 | E-102 | E-103 |
|---|---|---|---|---|
| $T_{Out}$ ° C. (1$^{st}$ stream) | 80 (S7) | 350 (S4) | 148 (S9) | 350 |
| $T_{Out}$ ° C. (2$^{nd}$ stream) | 324 (S3) | Steam | 210 (S10) | Steam |
| Calculated Heat Duty MJ/h | 5867 | 404 | 1418 | 1161 |

Table 5 shows design parameters of the distillation columns. Acetone is separated as a gas in column C-100 and recycled back to reactor R-100. Column C-101 and column C102 operate at total condenser mode in which distillate is produced in liquid phase. The reflux ratio is 1.3 for all columns where cooling water is used for condensation.

TABLE 5

| Distillation Column | C-100 | C-101 | C-102 |
|---|---|---|---|
| Condenser type | Partial | Total | Total |
| R/Rmin | 1.3 | 1.3 | 1.3 |
| Number of stages | 54 | 22 | 67 |
| Condenser duty MJ/h | −8573 | −1505 | −5300 |
| Reboiler duty MJ/h | 10521 | 2437 | 5371 |
| Calc. Reflux ratio | 11.77 | 2.8 | 4.3 |
| Column pressure drop (atm) | 0.5 | 0.5 | 0.5 |

Example 2

The calculation of example 1 was repeated for an acetone feed (mixed acetone) that enters as gas phase (vapor fraction=1) with a temperature of 75° C. and pressure of 1.8 atm. All process conditions were as in Example 1. For this case, the temperature of acetone may be increased in unit E-100 to 340° C. The heat load of E-101 is decreased since acetone feed (mixed acetone) temperature is only raised by 10° C. Table 6 shows the heat duties of heat exchangers in the gas-phase section. The outlet temperature of reactor effluent is about 198° C. which is not suitable as an input temperature to the compressor. Therefore, a heat exchanger may be required before to the compressor. This shows that it is superior to enter the fresh acetone feed (mixed acetone) as a liquid stream.

TABLE 6

| Heat Exchanger | E-100 | E-101 | E-102 | E-103 |
|---|---|---|---|---|
| $T_{Out}$ ° C. (1$^{st}$ stream) | 198 (S7) | 350 (S4) | 148 (S9) | 350 |
| $T_{Out}$ ° C. (2$^{nd}$ stream) | 340 (S3) | Steam | 210 (S10) | Steam |
| Calculated Heat Duty MJ/h | 3498 | 158.4 | 1418 | 1161 |

Example 3

The calculations of Example 1 were repeated with a reactor temperature of 300° C. and atmospheric pressure, to provide a direct comparison with Example 1. The catalyst used for the simulation is nano-Pd/nano-ZnCr$_2$O$_4$ with acetone conversion of 66% and MIBK selectivity of 69.4%. All stream numbers correspond to FIG. 2 and FIG. 3. The results of the calculations are summarized in Table 7, Table 8 and Table 9.

TABLE 7

| | S1 | S2 | S3 | S4 | S6 | S8 |
|---|---|---|---|---|---|---|
| | \multicolumn{6}{c}{Stream No.} | | | | | |

| | S1 | S2 | S3 | S4 | S6 | S8 |
|---|---|---|---|---|---|---|
| Molar flow kmol/h | 100 | 145.8 | 145.8 | 145.8 | 403.4 | 403.4 |
| Mass flow kg/h | 5808 | 8390.7 | 8390.3 | 8390.3 | 9545.4 | 9545.4 |
| Temp C. | 70 | 74.2 | 270 | 300 | 300 | 224.1 |
| Pressure atm | 1.8 | 1.8 | 1.4 | 1.2 | 1 | 6.5 |
| Vapor mole fraction | 0 | 0.3034 | 1 | 1 | 1 | 1 |
| Component mole % | | | | | | |
| Hydrogen | 0 | 0.02 | 0.02 | 0.02 | 61.35 | 61.35 |
| Acetone | 100 | 98.66 | 98.66 | 98.66 | 12.71 | 12.71 |

TABLE 7-continued

| | Stream No. | | | | | |
|---|---|---|---|---|---|---|
| | S1 | S2 | S3 | S4 | S6 | S8 |
| MIBK | 0 | 0 | 0 | 0 | 8.73 | 8.73 |
| Water | 0 | 1.33 | 1.33 | 1.33 | 12.53 | 12.53 |
| Diacetone Alcohol(DA) | 0 | 0 | 0 | 0 | 0.28 | 0.28 |
| Mesityl Oxide (MO) | 0 | 0 | 0 | 0 | 0.26 | 0.26 |
| Mesitylene (M) | 0 | 0 | 0 | 0 | 0.22 | 0.22 |
| Isopropanol (IPA) | 0 | 0 | 0 | 0 | 2.88 | 2.88 |
| Diisobutyl Ketone (DIBK) | 0 | 0 | 0 | 0 | 1.02 | 1.02 |

TABLE 8

| | Stream No. | | | | | |
|---|---|---|---|---|---|---|
| | S9 | S10 | S11 | S13 | S14 | S15 |
| Molar flow kmol/h | 403.4 | 312.1 | 312.1 | 403.4 | 257.9 | 53.9 |
| Mass flow kg/h | 9545.4 | 1155.9 | 1155.9 | 9545.4 | 1046 | 108.7 |
| Temp C. | 174.1 | 165 | 300 | 35 | 35 | 25 |
| Pressure atm | 6.1 | 5.5 | 5.2 | 5.9 | 5.9 | 5.9 |
| Vapor mole fraction | 1 | 1 | 1 | 0.6392 | 1 | 1 |
| Component mole % | | | | | | |
| Hydrogen | 61.35 | 96.66 | 96.66 | 61.35 | 95.97 | 100 |
| Acetone | 12.71 | 2.24 | 2.24 | 12.71 | 2.71 | 0 |
| MIBK | 8.73 | 0.22 | 0.22 | 8.73 | 0.27 | 0 |
| Water | 12.53 | 0.71 | 0.71 | 12.53 | 0.86 | 0 |
| Diacetone Alcohol (DA) | 0.28 | 0 | 0 | 0.28 | 0 | 0 |
| Mesityl Oxide (MO) | 0.26 | 0 | 0 | 0.26 | 0 | 0 |
| Mesitylene (M) | 0.22 | 0 | 0 | 0.22 | 0 | 0 |
| Isopropanol (IPA) | 2.88 | 0.15 | 0.15 | 2.88 | 0.18 | 0 |
| Diisobutyl Ketone (DIBK) | 1.02 | 0 | 0 | 1.02 | 0.01 | 0 |

TABLE 9

| | Stream No | | | | | |
|---|---|---|---|---|---|---|
| | S18 | S20 | S23 | S24 | S27 | S29 |
| Molar flow kmol/h | 145.5 | 99.7 | 57.9 | 16.5 | 34 | 7.5 |
| Mass flow kg/h | 8499.4 | 5916.7 | 5164.3 | 807.4 | 3399.1 | 957.8 |
| Temp C. | 35.1 | 107.2 | 70 | 92.8 | 145.9 | 193 |
| Pressure atm | 1.8 | 2.3 | 1.7 | 1.7 | 2.2 | 2.7 |
| Vapor mole fraction | 0.000148 | 0 | 0 | 0 | 0 | 0 |
| Component mole % | | | | | | |
| Hydrogen | 0.02 | 0 | 0 | 0 | 0 | 0 |
| Acetone | 30.44 | 0.44 | 0.76 | 2.69 | 0 | 0 |
| MIBK | 23.74 | 34.64 | 59.62 | 2.1 | 99.64 | 4.56 |
| Water | 33.22 | 46.54 | 8.01 | 28.18 | 0 | 0 |
| Diacetone Alcohol (DA) | 0.79 | 1.15 | 1.98 | 0 | 0 | 15.27 |
| Mesityl Oxide (MO) | 0.72 | 1.05 | 1.8 | 0 | 0.03 | 13.79 |
| Mesitylene (M) | 0.59 | 0.87 | 1.49 | 0 | 0 | 11.51 |
| Isopropanol (IPA) | 7.66 | 11.18 | 19.24 | 67.03 | 0.33 | 0 |
| Diisobutyl Ketone (DIBK) | 2.83 | 4.13 | 7.1 | 0 | 0 | 54.87 |

Example 4

Numerous catalysts were investigated for one-step gas-phase production of MIBK to obtain high yield. Very promising nano catalysts have been validated for high conversion of acetone at atmospheric pressure. This invention presents a process for manufacturing MIBK and other products via low-pressure one-step gas-phase acetone self-condensation. The novel catalyst which is used as an example is nano-crystalline zinc chromite supported nano-palladium (nano-Pd/nano-$ZnCr_2O_4$). The production of MIBK is carried out at atmospheric pressure inside the reactor (e.g. fixed-bed catalytic reactor) with a temperature ranges between 200° C. and 350° C. The feed hydrogen-acetone ratio may range between 1 to 6 mole ratios. The nano-Pd/nano-$ZnCr_2O_4$ catalyst provides high conversion of acetone and high selectivity towards MIBK when operated at high temperatures.

The low-pressure one-step gas-phase process has advantages over the one-step liquid phase process when using selective catalysts such as nano Pd/nano-$ZnCr_2O_4$. The reactor is operated at atmospheric pressure or low pressure while other plant unit operations are operated at low pressures. This scheme eventually reduces capital and operating costs of MIBK production process.

Table 10 shows some experimental kinetic data of nano Pd/nano-$ZnCr_2O_4$ catalyst for manufacturing MIBK from acetone and hydrogen via one-step gas-phase process at atmospheric pressure. Other products which are produced along with MIBK include diisobutyle ketone (DIBK), isopropyl alcohol (IPA), mesityl oxide (MO), mesitylene (M) and diacetone alcohol (DA). The high conversion of acetone and good selectivity towards MIBK at high temperatures decrease quantities of other by products which may cause complicity in the separation section of the process. The gas-phase single-step process with high conversion and selectivity makes the process very cost effective.

TABLE 10

| Temp (° C.) | Acetone Conv. % | Selectivity % | | | | | |
|---|---|---|---|---|---|---|---|
| | | MIBK | DIBK | MO | M | IPA | DA & others |
| 200 | 20.1 | 40.6 | 10.2 | 6.1 | 2.1 | 40.7 | 0.3 |
| 250 | 40.7 | 53.9 | 12.3 | 4.4 | 2.5 | 25.8 | 1.1 |
| 300 | 66 | 69.4 | 12.4 | 2.1 | 2.6 | 11.2 | 2.3 |
| 350 | 77.3 | 72.1 | 13.5 | 2.2 | 2.7 | 5.4 | 4.1 |

In addition, the specification and drawings are to be regarded in an illustrative rather than as in a restrictive sense.

What is claimed is:

1. A method, comprising;
    adding a mixed acetone and a mixed hydrogen stream to a reactor containing a nano-ZnO catalyst to perform low-pressure one-step gas-phase condensation of the acetone for making a product;
    providing pressure to the mixed acetone and mixed hydrogen before entering the reactor;
    recycling the acetone recovered from the reactor back to the reactor for reuse as a recycled acetone; and
    heating the mixed acetone with a heat exchanger before reintroducing it to the reactor.

2. The method of claim 1, further comprising;
    removing the water content in the recycled acetone by using a dryer; fractionating the reactor effluent using series of distillation columns to recover the by products of acetone and hydrogen condensation.

3. The method of claim 1, wherein the fractions as by products are at least one of methyl isobutyl ketone, diisobutyl ketone, mesityl oxide, mesitylene, isopropyl alcohol and other products.

4. The method of claim 1, wherein the catalyst is nano-crystalline zinc, chromite supported nano-palladium (nano-Pd/nano-ZnCr$_2$O$_4$).

5. The method of claim 1, wherein the temperature is between 200-350° C.

6. The method of claim 1, wherein the pressure is to at least one of atmospheric pressure and low pressure.

7. A one-step gas-phase process, comprising;
    producing a product from acetone and hydrogen using a nano-ZnO catalyst;
    recovering the heat of a reactor effluent to raise a temperature of a recycled acetone stream and a fresh feed acetone stream;
    passing the fresh acetone stream and the recycled acetone stream as a mixture in a heat exchanger to efficiently manage a temperature of a mixed acetone before it enters the reactor; and
    modulating the pressure of the mixed acetone feed (mixed acetone) by passing it through a pressure valve having at least one of an atmospheric pressure and low pressure.

8. The one-step gas-phase process of claim 7, further comprising;
    preheating the mixture of a recycled hydrogen and a fresh hydrogen in a heat exchanger;
    and regulating the pressure to at least one of atmospheric pressure and low pressure of the mixed hydrogen before entering the reactor.

9. The one-step gas-phase process of claim 8, further comprising;
    compressing the reactor effluent to a low pressure in a compressor before sending it to the second heat exchanger; and
    enabling the efficient separation of hydrogen in the drum by compressing and cooling the reactor effluent.

10. The one-step gas-phase process of claim 7, wherein the catalyst is nano-crystalline zinc chromite supported nano-palladium (nano-Pd/nano-ZnCr$_2$O$_4$).

11. The one-step gas-phase process of claim 7, wherein the products are at least one of methyl isobutyl ketone, diisobutyl ketone, mesityl oxide, mesitylene and isopropyl alcohol.

12. The one-step gas-phase process of claim 7, wherein the temperature is between 200-350° C.

* * * * *